(12) United States Patent
Bouasaysy et al.

(10) Patent No.: US 11,504,142 B2
(45) Date of Patent: Nov. 22, 2022

(54) RE-ENTRY CATHETER

(71) Applicant: ReFlow Medical, Inc., San Clemente, CA (US)

(72) Inventors: Outhit Bouasaysy, Corona, CA (US); John Fulkerson, Rancho Santa Margarita, CA (US); Isa Rizk, San Diego, CA (US); Fadi Saab, Ada, MI (US)

(73) Assignee: ReFlow Medical, Inc., San Clemente, CA (US)

( * ) Notice: Subject to any disclaimer, the term of this patent is extended or adjusted under 35 U.S.C. 154(b) by 0 days.

(21) Appl. No.: 16/993,145

(22) Filed: Aug. 13, 2020

(65) Prior Publication Data

US 2021/0045757 A1 Feb. 18, 2021

Related U.S. Application Data

(60) Provisional application No. 62/886,239, filed on Aug. 13, 2019.

(51) Int. Cl.
| | |
|---|---|
| *A61B 17/22* | (2006.01) |
| *A61M 25/00* | (2006.01) |
| *A61M 25/09* | (2006.01) |
| *A61M 25/01* | (2006.01) |

(52) U.S. Cl.
CPC .......... *A61B 17/22* (2013.01); *A61M 25/007* (2013.01); *A61M 25/09* (2013.01); *A61B 2017/22038* (2013.01); *A61M 25/0108* (2013.01)

(58) Field of Classification Search
CPC ......... A61B 17/22; A61B 2017/22038; A61M 25/007; A61M 25/0108; A61M 25/0194; A61M 25/09; A61M 2025/0018; A61M 2025/0183; A61M 2025/0197
See application file for complete search history.

(56) References Cited

U.S. PATENT DOCUMENTS

| | | | | |
|---|---|---|---|---|
| 4,552,554 | A * | 11/1985 | Gould | A61M 25/01 604/104 |
| 6,585,650 | B1 * | 7/2003 | Solem | A61F 2/064 600/438 |
| 7,179,270 | B2 | 2/2007 | Makower | |
| 10,098,650 | B2 | 10/2018 | Kangas et al. | |
| 2001/0000041 | A1 * | 3/2001 | Selmon | A61B 17/3207 600/585 |
| 2003/0045836 | A1 * | 3/2003 | Batiste | A61M 25/01 604/164.13 |
| 2003/0153934 | A1 * | 8/2003 | Gerberding | A61M 25/0169 606/157 |

(Continued)

OTHER PUBLICATIONS

International Search Report and Written Opinion from PCT/US2020/046232, dated Dec. 3, 2020, 17 pages.

*Primary Examiner* — Jocelin C Tanner
(74) *Attorney, Agent, or Firm* — BakerHostetler

(57) ABSTRACT

A delivery system can be provided with an ability to change its configurations to achieve both access to target anatomy and treatment thereof. Such treatments can include directing interventional devices around an occlusion. By providing different functionality at different stages, the need to exchange and replace tools at different stages can be reduced or eliminated. Accordingly, such operations can be completed more rapidly, efficiently, and safely.

20 Claims, 4 Drawing Sheets

(56) References Cited

U.S. PATENT DOCUMENTS

| | | | |
|---|---|---|---|
| 2006/0036233 A1* | 2/2006 | Boutillette | A61M 25/00 604/528 |
| 2006/0047335 A1* | 3/2006 | Israel | A61F 2/954 623/1.11 |
| 2006/0276749 A1* | 12/2006 | Selmon | A61B 6/12 604/164.01 |
| 2009/0182200 A1* | 7/2009 | Golden | A61M 25/0052 600/153 |
| 2012/0095485 A1 | 4/2012 | Cully et al. | |
| 2018/0056046 A1* | 3/2018 | Kiersey | A61F 2/2427 |
| 2018/0333162 A1 | 11/2018 | Saab | |
| 2019/0134349 A1* | 5/2019 | Cohn | A61M 25/0021 |
| 2020/0129143 A1 | 4/2020 | Di Tullio et al. | |

\* cited by examiner

RE-ENTRY CATHETER

CROSS-REFERENCE TO RELATED APPLICATION

This application claims the benefit of U.S. Provisional Application No. 62/886,239, entitled "RE-ENTRY CATHETER," filed Aug. 13, 2019, the entirety of which is incorporated herein by reference.

TECHNICAL FIELD

The present description relates in general to treatment of stenosis in a body vessel and in particular to catheters and methods for crossing a chronic total occlusion in a blood vessel.

BACKGROUND OF THE DISCLOSURE

Chronic total occlusions ("CTO") are vascular lesions characterized by heavy atherosclerotic plaque within the blood vessel, resulting in complete (or nearly complete) obstruction of blood flow across the lesion. Such occlusions can occur anywhere in a patient's vascular system. Since most lesions form gradually over a long period of time, the ischemic tissue downstream of the lesion has time to form collateral circulation. For example, in the case of coronary arteries, collateral vessels can form from the proximal artery and connect into the distal artery ("ipsilateral collaterals"), or collateral vessels can form from the other major arterial branches and connect into the distal artery ("contralateral collaterals"). When the lesion finally becomes a total occlusion, the collateral circulation is typically sufficient to keep the distal tissue alive, though ischemic. Accordingly, it is desirable to reestablish blood flow through or around the blockage in blood vessels by crossing the CTO and advancing therapeutic devices, such as a balloon angioplasty catheter, to dilate and treat the CTO. Likewise, in some cases it may be necessary to cross a CTO to gain access to a location along the vasculature distal to the CTO. CTOs can be more difficult to cross than partially occluded lesions because, rather than navigate a pre-existing lumen, a guidewire must either penetrate the lesion or, when penetrating the occlusion is impractically difficult and/or complicated, go around the lesion via a sub-intimal layer of a vessel wall.

The description provided in the background section should not be assumed to be prior art merely because it is mentioned in or associated with the background section. The background section may include information that describes one or more aspects of the subject technology.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The present technology relates generally to systems, methods, and devices for crossing and treating CTOs. While CTOs are discussed, it will be understood that the devices and methods described herein can facilitate treatment of a variety of conditions.

It can be desirable to provide a system and/or devices that facilitate access to target anatomy (e.g., CTO in a blood vessel) and further facilitate an intervention for restoring flow across the CTO. Various stages of such operations may involve the operation of multiple tools to access, cross, and treat the target anatomy. The systems and methods described herein are directed to devices that provide multiple functions at different stages. By providing different functionality at different stages, the need to exchange and replace tools at different stages can be reduced or eliminated. Accordingly, such operations can be completed more rapidly, efficiently, and safely.

Specific details of several embodiments of the present technology are described herein with reference to FIGS. 1-11. Although many of the embodiments are described below with respect to devices and methods for crossing and/or treating CTOs, any vascular occlusion in addition to those described herein may be crossed and/or treated within the scope of the present technology (e.g., full occlusions, partial occlusions, occlusions resulting from a thrombus, occlusions resulting from an embolism, occlusions resulting from atherosclerosis, etc.). Additionally, other embodiments of the present technology can have different configurations, components, or procedures than those described herein. For example, other embodiments can include additional elements and features beyond those described herein, or other embodiments may not include several of the elements and features shown and described herein.

Figure 1:
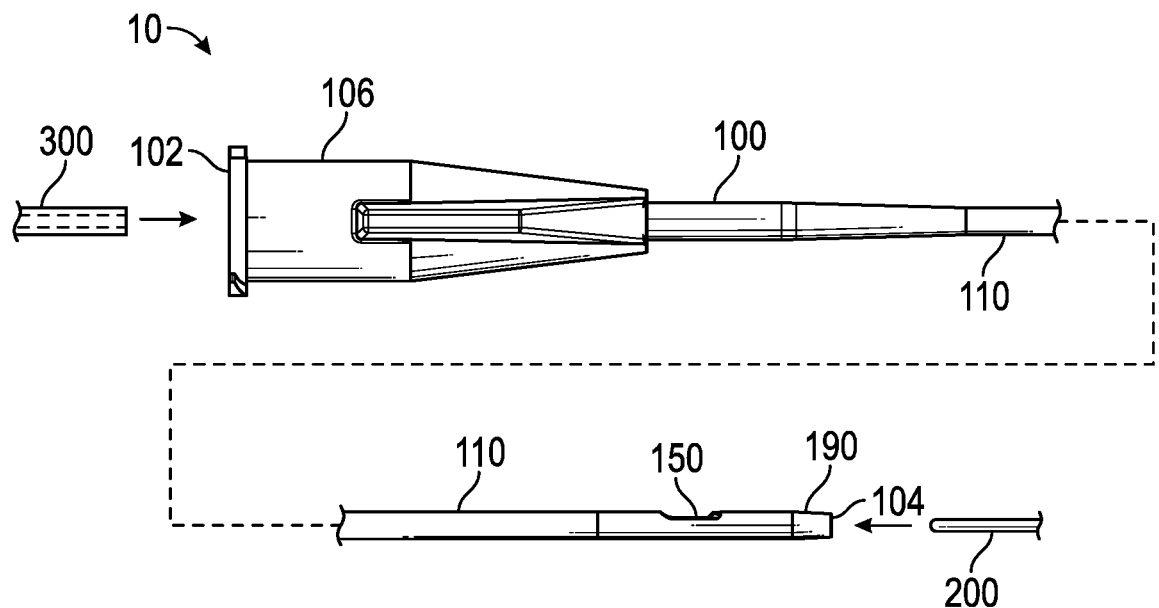
FIG. 1 illustrates a side view of a delivery device.

As shown in FIG. 1, a system can include a delivery device 100 for delivering another device through a lumen thereof. The delivery device 100 can include a connector 106 at and/or defining a proximal end portion 102 of the delivery device 100 and providing a handle, luer, connector, and/or hub. For example, the connector 106 can include a mating feature and/or a receiving feature for securely coupling to other components. The connector 106 can include a touhy bourst seal configured to secure a position of one or more devices within the delivery device 100.

The delivery device 100 can further include a distal tip 190 at and/or defining a distal end portion 104 of the delivery device 100. The distal tip 190 can include a radiopaque distal tip (e.g., polymer, tungsten, barium, etc.). The delivery device 100 can further include a shaft 110 extending between the connector 106 and the distal tip 190. The connector 106 can be configured to be positioned at a location external to a patient, and the shaft 110 can be configured to position the distal tip 190 (e.g., intravascularly) at or near a complete or partial occlusion within a blood vessel of the patient. The delivery device 100 can have a lumen extending from the connector 106 to the distal tip 190 and/or a side port 150. The delivery device 100 can include a strain relief element between the shaft 110 and another portion at the connector 106. For example, the strain relief element can surround or otherwise engage the shaft 110 at a proximal end thereof.

The delivery device 100 can receive one or more devices (e.g., guidewire 200) into the lumen through the distal end portion 104. The delivery device 100 can receive one or more devices (e.g., crossing device 300) into the lumen through the proximal end portion 102.

The shaft 110 can be sized and shaped for intravascularly accessing a target site (e.g., treatment site) of the patient. In some embodiments, for example, the shaft 110 has a length of about 150 cm to about 180 cm and a suitable cross-sectional dimension for positioning within a subject's vasculature. The length of the shaft 110 can be a working length, such as a length that can be positioned within a subject's vasculature. In some embodiments, for example, the working length is about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm.

Figure 2:
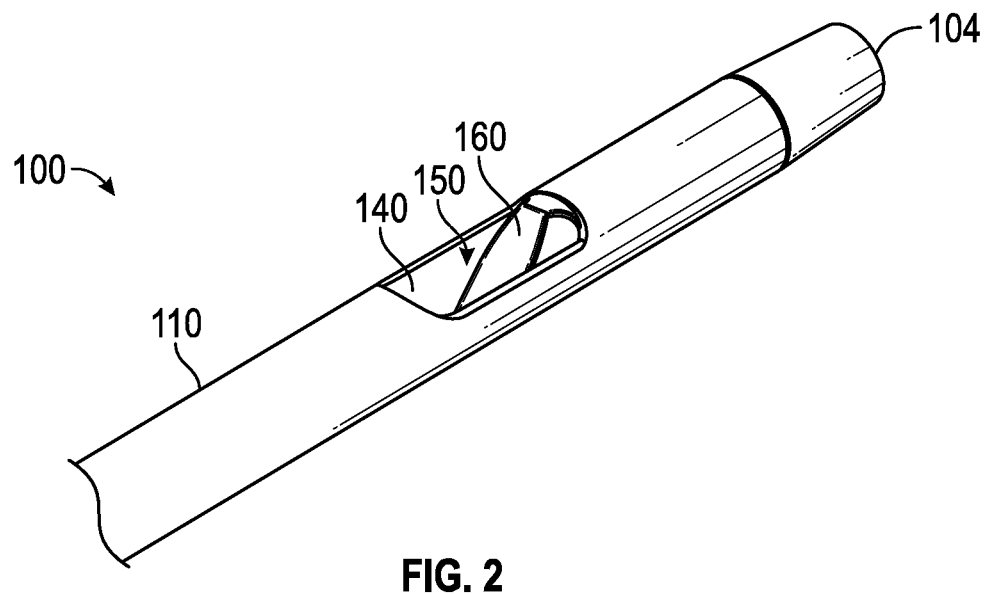
FIG. 2 illustrates a perspective view of a distal portion of a delivery device.
Figure 3:
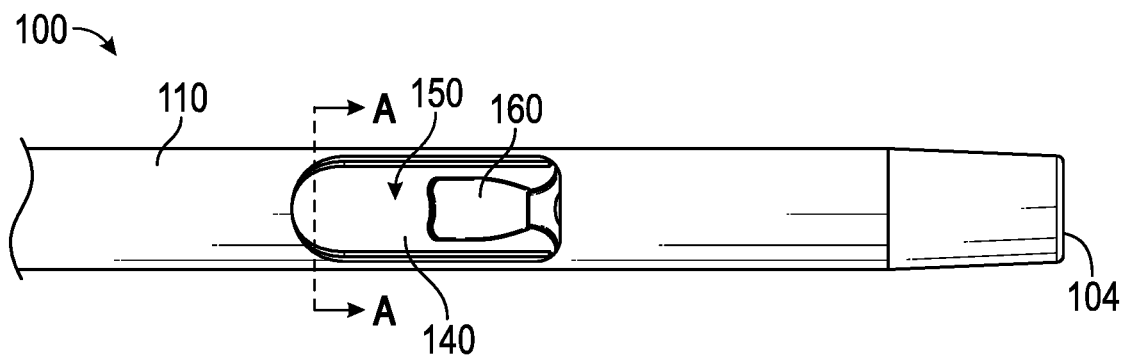
FIG. 3 illustrates a top view of a distal portion of a delivery device.
Figure 4:
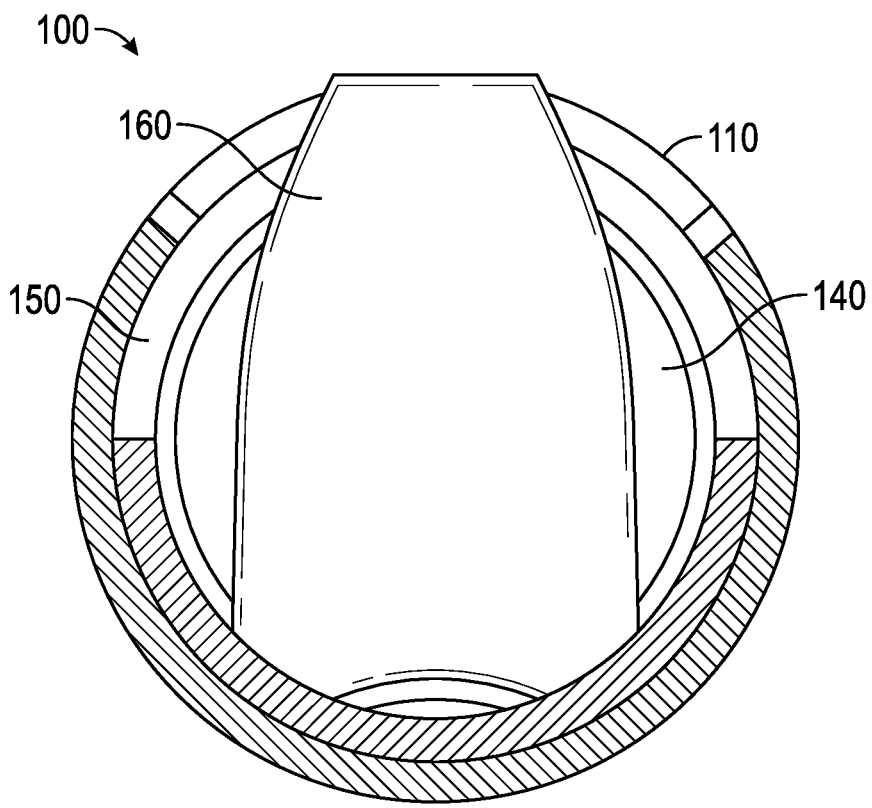
FIG. 4 illustrates a sectional view of a distal portion of a delivery device, taken along line A-A of FIG. 3.

Referring now to FIGS. 2-4, the shaft 110 can be or include a catheter shaft lined with an inner layer (e.g., PTFE, hydrophilic coating, etc.) and/or jacketed with on outer layer (e.g., polymers, stainless steel braiding, polyimide, etc.). The side port 150 can be formed in the shaft 110 at a location between the proximal end and the distal end portion 104 of the delivery device 100. The side port 150 connects the lumen 140 to a space laterally adjacent to the shaft 110. The side port 150 can be molded, laser cut or otherwise formed into the shaft 110.

As shown in FIGS. 2 and 3, a flap member 160 can be positioned at or near the side port 150. For example, the flap member 160 can extend from a portion of the shaft 110 that is adjacent to the side port 150. The flap member 160 can at least partially extend into the lumen 140 and at least one configuration thereof. The flap member 160 can be integrally formed (e.g., monolithic) with at least a portion of the shaft 110 and/or securely coupled thereto. As used herein, a monolithic structure is one that is integrally formed of a single piece of material, rather than of separate pieces that are joined together by an interface. For example, the flap member 160 and the shaft 110 can be a unibody and/or unitary structure. By providing a monolithic, unitary, and/or unibody flap member 160 and shaft 110, these components need not contain interfaces or discontinuities, such as those that occur in assembled parts. Accordingly, the monolithic, unitary, and/or unibody flap member 160 and shaft 110 can be fabricated to more precise and consistent dimensions as well as provide greater structural support.

The flap member 160 can include a metal, such as a shape memory alloy (e.g., Nitinol). The flap member 160 can be heat set (e.g., annealed) into a position and/or configuration such that it is biased to such a configuration (e.g., first position) in the absence of an external force that deflects the flap member 160.

As shown in FIG. 4, in at least one configuration, the flap member 160 can extend from the shaft 110 into the lumen 140. The flap member 160 can block at least a portion of the lumen 140 for objects traveling along the longitudinal axis 108 of the delivery device 100 (e.g., within the lumen 140). The flap member 160 can be positioned and shaped to allow objects to stay within the lumen 140 when crossing the flap member 160 when such objects approach the flap member 160 from one side thereof. The flap member 160 can be positioned and shaped to deflect objects out of the lumen 140 and through the side port 150 when crossing the flap member 160 when such objects approach the flap member 160 from another side thereof.

As further shown in FIG. 4, the flap member 160 can include a terminal end that facilitates interaction with and passage of a guidewire 200 or other interventional device. For example, the terminal end can include a concave shape that receives a portion of the guidewire 200. Such a shape can help direct the guidewire 200 to a preferred position with respect to the flap member 160 and maintain the guidewire 200 in a particular position within the lumen 140 (e.g., radially and/or circumferentially) while the guidewire 200 travels longitudinally within the lumen 140.

Figure 5:
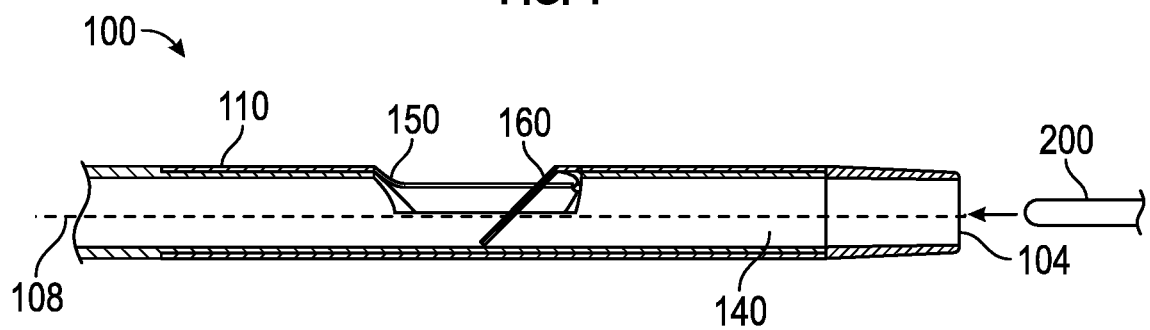
FIG. 5 illustrates a side sectional view of a delivery device and a guidewire.

Referring now to FIGS. 5-8, the delivery device 100 can be operated to facilitate positioning of other devices with respect to a body vessel and/or objects therein (e.g., CTO). As shown in FIG. 5, a guidewire 200 can be inserted through the distal end portion 104 of the delivery device 100. As the guidewire 200 passes the flap member 160, the flap member 160 can deflect as needed to allow passage of the guidewire 200 through the lumen 140 and beyond the flap member 160. Furthermore, the flap member 160 can maintain the guidewire 200 within the lumen 140 and prevent the guidewire 200 from exiting the shaft 110 through the side port 150. As such the guidewire 200 can be directed to the proximal end of the delivery device 100 for operation by a user at the proximal end.

Figure 6:
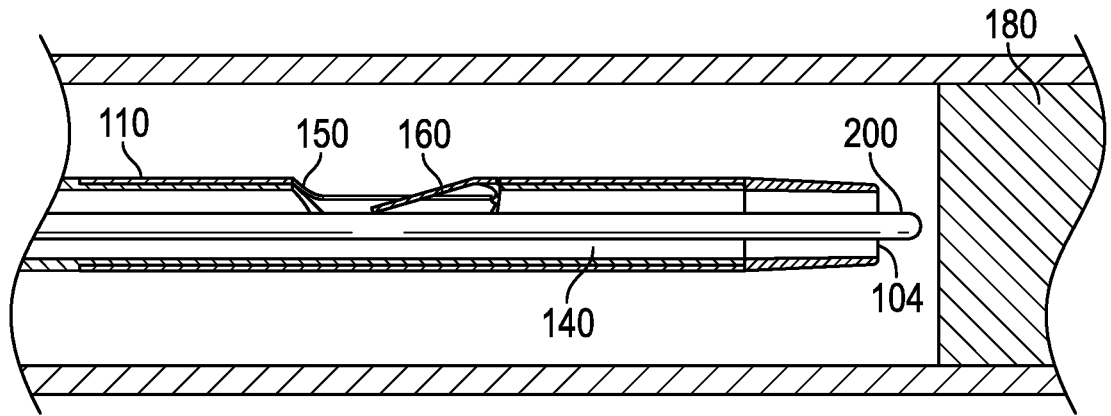
FIG. 6 illustrates a side sectional view of the delivery device in a body vessel with the guidewire extending out a distal end of the delivery device.

As shown in FIG. 6, the delivery device 100 and the guidewire 200 can be positioned within an anatomy of the patient (e.g., within a blood vessel and adjacent to an occlusion 180). At least a portion of the guidewire 200 can remain within the lumen 140 and distal to the flap member 160. As such, the flap member 160 can remain in a deflected (e.g., second) position. The guidewire 200 can be operated to penetrate the occlusion. Additionally or alternatively, another device (e.g., coupled to the guidewire 200 and/or inserted through the proximal end of the delivery device) can be operated to penetrate the occlusion. The guidewire 200 and/or another device can be moved within the lumen 140 and maintain a position partially distal to the flap member 160 by limiting its proximally directed retraction.

Figure 7:
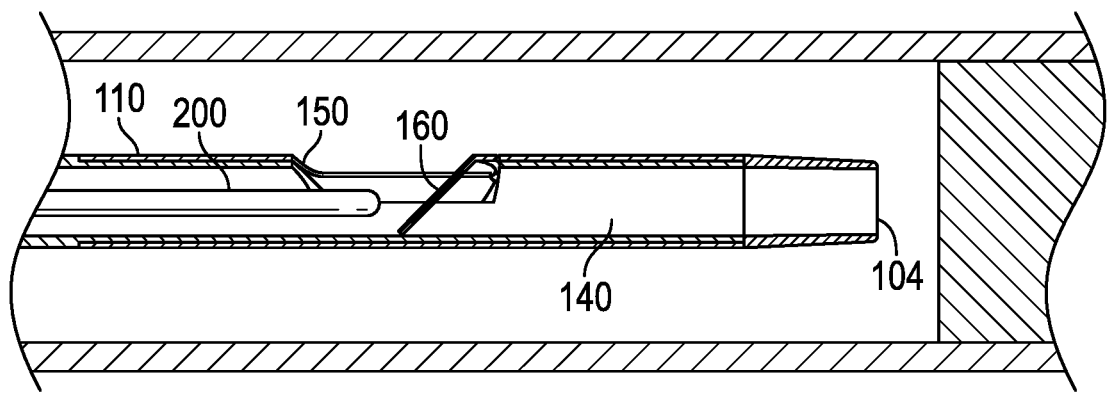
FIG. 7 illustrates a side sectional view of the delivery device with the guidewire retracted proximally within the delivery device.

As shown in FIG. 7, the guidewire 200 can be operated to facilitate sub-intimal penetration and/or crossing of the occlusion. The guidewire 200 can be retracted proximally to be entirely proximal to the flap member 160. When the guidewire 200 is no longer spanning the flap member 160, the flap member 160 can return to a biased (e.g., first) position, in which it blocks at least a portion of the lumen 140.

Figure 8:
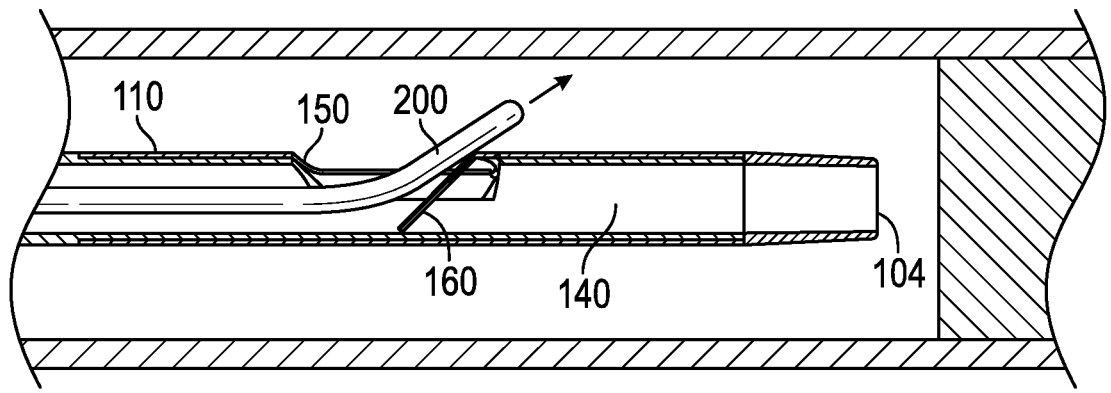
FIG. 8 illustrates a side sectional view of the delivery device with the guidewire extending out of a side port of the delivery device.

As shown in FIG. 8, the flap member 160 can direct the guidewire 200 through the side port 150. The guidewire 200 can be advanced distally until it contacts the flap member 160. The flap member 160, in its biased position, can provide a surface that directs the guidewire 200 away from the lumen 140, through the side port 150, and toward the vessel wall. For example, the flap member 160 can form an oblique (i.e., neither parallel nor perpendicular) angle with respect to the longitudinal axis 108 of the shaft 110. Accordingly, by advancing the guidewire 200 longitudinally against the flap member 160, the flap member 160 redirects the guidewire 200 out of the side port 150 and in a direction that forms an oblique angle with respect to the longitudinal axis 108 of the shaft 110.

The guidewire 200 can be operated to penetrate the vessel wall. Additionally or alternatively, another device (e.g., coupled to the guidewire 200 and/or inserted through the proximal end of the delivery device) can be operated to penetrate the vessel wall. Such penetration can allow the guidewire 200 to travel around the occlusion 180, thereby providing access to an opposite side thereof. Such access can be used to restore and enhance flow across the occlusion 180.

Additionally or alternatively, the guidewire 200 can be used with or replaced by an interventional device in one or more of the steps described herein and/or in an additional step. An example of such an interventional device is the crossing device disclosed in International Patent Application No. PCT/US2010/047170, filed Aug. 30, 2010, entitled "SYSTEMS, METHODS AND DEVICES FOR ABLATION, CROSSING, AND CUTTING OF OCCLUSIONS," which is incorporated herein by reference in its entirety. For example, an interventional device can be actuated (e.g., advanced, retracted, rotated, etc.) and provide features (e.g., blades, edges, cutting implements, etc.) that facilitate penetration or other actions with respect to the target anatomy (e.g., CTO, vessel wall, etc.).

A delivery device can include any number of side ports 150 and flap members 160. The different side ports 150 and flap members 160 can be proximal to, distal to, and/or axially overlapping each other. The different side ports 150 and flap members 160 can be on a same or different radial side with respect to each other. Devices (e.g., guidewires, interventional devices, etc.) extending through different side ports can extend through the same proximal end and/or lumen of a shaft or through different locations.

Figure 9:
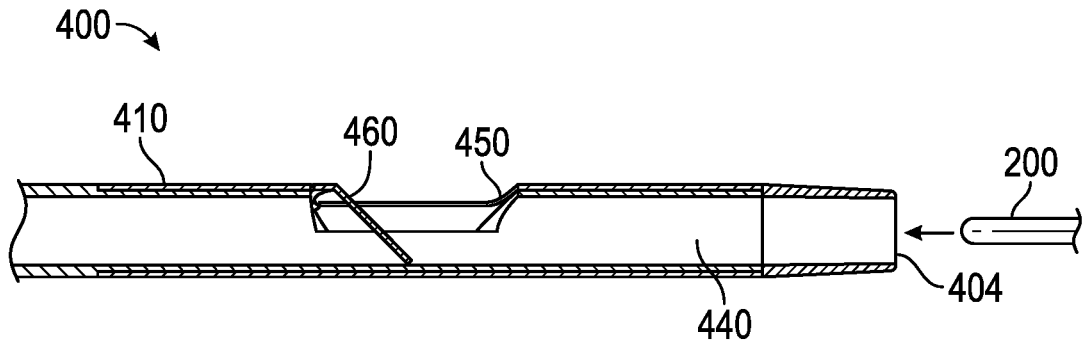
FIG. 9 illustrates a side sectional view of a delivery device and a guidewire in a rapid exchange configuration.
Figure 10:
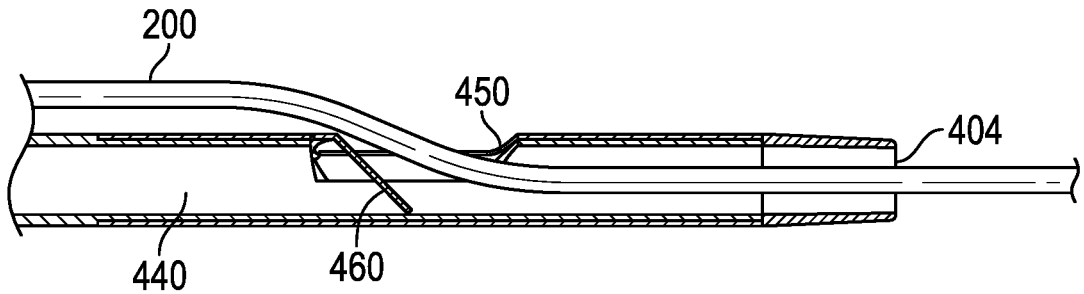
FIG. 10 illustrates a side sectional view of the delivery device with the guidewire extending through a distal end and a side port of the delivery device.
Figure 11:
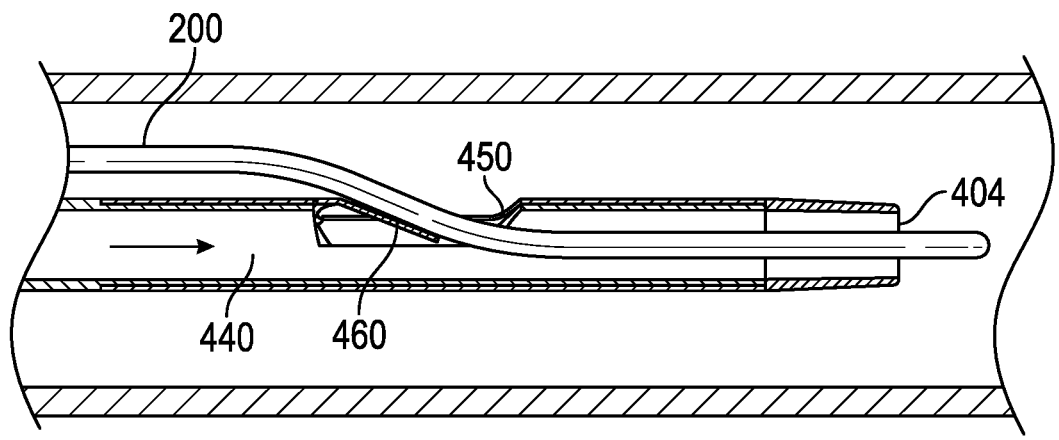
FIG. 11 illustrates a side sectional view of the delivery device in a body vessel with the guidewire extending through the distal end and the side port of the delivery device.

Referring now to FIGS. 9-11, a delivery device 400 can be operated to facilitate operation of devices and/or fluid flow with respect to a body vessel and/or objects therein (e.g., CTO). As shown in FIG. 9, a guidewire 200 can be inserted through the distal end 404 of the delivery device 400. Such an operation can be performed while the delivery device 400 is outside the patient.

As shown in FIG. 10, the flap member 460 can direct the guidewire 200 through the side port 450. The guidewire 200 can be advanced proximally until it contacts the flap member 460. The flap member 460, in its biased position, can provide a surface that directs the guidewire 200 away from the lumen 440 and through the side port 450.

As shown in FIG. 11, the delivery device 400, along with the guidewire 200, can be positioned within an anatomy (e.g., blood vessel) of the patient.

At least a portion of the guidewire 200 can remain within the lumen 140 and distal to the flap member 160. The guidewire 200 and/or another device can be moved within the lumen 140 and/or alongside the shaft 410.

Fluid can be provided through the lumen 440 for injection into the target anatomy. For example, the fluid can be provided at the proximal end of the delivery device 400 and through the lumen 440. As the flow of fluid is incident upon the flap member 460, the flap member 460 can deflect as needed to allow passage of the fluid through the lumen 440 and beyond the flap member 460. Furthermore, the flap member 460 can maintain at least some of the fluid within the lumen 440 and prevent at least some of the fluid from exiting the shaft 410 through the side port 450. As such the fluid can be directed to the distal end 404 of the delivery device 400 for injection. Such operations can be performed while the guidewire 200 and/or another device remains at least partially within the lumen 440 (e.g., distal to the flap member 460 and/or the side port 450).

A delivery device can include any number of side ports 450 and flap members 460. The different side ports 450 and flap members 460 can be proximal to, distal to, and/or axially overlapping each other. The different side ports 450 and flap members 460 can be on a same or different radial side with respect to each other. Devices (e.g., guidewires, interventional devices, etc.) extending through different side ports can extend through the same distal end and/or lumen of a shaft or through different locations.

While the delivery device 100 and the delivery device 400 are shown as separate devices, it will be understood that a single delivery device can include one or more of each of a side port 150, a flap member 160, a side port 450, and/or a flap member 460. The side port 150 and the flap member 160 can be proximal to, distal to, and/or axially overlapping the side port 450 and the flap member 460. The side port 150 and the flap member 160 can be on a same or different radial side with respect to that of the side port 450 and the flap member 460.

Vessels in which the delivery devices described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Other vessels are likewise contemplated, and the delivery devices can be formed and/or selected according to a known destination and/or travel pathway within the body of a patient.

Accordingly, the systems and methods described herein provide multiple functions at different stages. By providing different functionality at different stages, the need to exchange and replace tools at different stages can be reduced or eliminated. Accordingly, such operations can be completed more rapidly, efficiently, and safely.

Various examples of aspects of the disclosure are described below as clauses for convenience. These are provided as examples, and do not limit the subject technology.

Clause A: a delivery device comprising: a proximal end; a distal end; a shaft defining a lumen extending between the proximal end and the distal end; a side port extending through the shaft at a portion of the shaft that is between the proximal end and the distal end; and a flap member extending from the shaft on a distal side of the side port and toward the proximal end of the delivery device, the flap member being configured to transition from a first position blocking at least a portion of the lumen to a second position blocking at least a portion of the side port.

Clause B: a delivery device comprising: a proximal end; a distal end; a shaft defining a lumen extending between the proximal end and the distal end; a side port extending through the shaft at a portion of the shaft that is between the proximal end and the distal end; and a flap member extending from the shaft on a proximal side of the side port and toward the distal end of the delivery device, the flap member being configured to transition from a first position blocking at least a portion of the lumen to a second position blocking at least a portion of the side port.

Clause C: a method comprising: inserting a proximal portion of a guidewire through a distal end of a delivery device, into a lumen of the delivery device, and past a flap member of the delivery device; retracting the guidewire until a distal portion of the guidewire is proximal to the flap member; and advancing the guidewire until the flap member directs the distal portion of the guidewire out of the lumen and through a side port of the delivery device.

One or more of the above clauses can include one or more of the features described below. It is noted that any of the following clauses may be combined in any combination with each other, and placed into a respective independent clause, e.g., clause A, B, or C.

Clause 1: the flap member is biased toward the first position.

Clause 2: an interventional device extending within the lumen and across the side port, wherein the interventional device is retractable proximally to be entirely proximal to the flap member.

Clause 3: the flap member is biased toward the interventional device.

Clause 4: the interventional device is a guidewire.

Clause 5: while in the first position, the flap member extends from the side port to a wall of the shaft that is opposite the side port.

Clause 6: a terminal end of the flap member defines a concave shape.

Clause 7: the flap member forms an oblique angle with respect to a longitudinal axis of the shaft while in the first position.

Clause 8: an interventional device extending through the distal end of the delivery device, a length of the lumen that is distal to the side port, and the side port.

Clause 9: after the inserting and before the retracting: advancing the guidewire to a target anatomy; and advancing the delivery device over the guidewire to the target anatomy.

Clause 10: the flap member is biased to a first position blocking at least a portion of the lumen and away from a second position blocking at least a portion of the side port.

Clause 11: the inserting transitions the flap member from the second position to the first position.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

The invention claimed is:

1. A delivery device comprising:
    a proximal end;
    a distal end;
    a shaft defining a lumen extending between the proximal end and the distal end;
    a side port extending through the shaft at a portion of the shaft that is between the proximal end and the distal end; and
    a flap member extending from the shaft on a distal side of the side port and toward the proximal end of the delivery device, wherein a terminal end of the flap member defines a concave shape, the flap member being configured to transition from a first position blocking at least a portion of the lumen to a second position blocking at least a portion of the side port.

2. The delivery device of claim 1, wherein the flap member is biased toward the first position.

3. The delivery device of claim 1, further comprising an interventional device extending within the lumen and across the side port, wherein the interventional device is retractable proximally to be entirely proximal to the flap member.

4. The delivery device of claim 3, wherein the flap member is biased toward the interventional device.

5. The delivery device of claim 3, wherein the interventional device is a guidewire.

6. The delivery device of claim 1, wherein, while in the first position, the flap member extends from the side port to a wall of the shaft that is opposite the side port.

7. The delivery device of claim 1, wherein the flap member forms an oblique angle with respect to a longitudinal axis of the shaft while in the first position.

8. The delivery device of claim 1, wherein the flap member is monolithically formed with at least a portion of the shaft.

9. The delivery device of claim 1, wherein the flap member comprises a shape memory alloy.

10. The delivery device of claim 1, wherein the side port is a first side port and the flap member is a first flap member, the delivery device further comprising:
    a second side port extending through the shaft; and
    a second flap member extending from the shaft on a distal side of the second side port and toward the proximal end of the delivery device.

11. The delivery device of claim 10, wherein the first side port and the second side port are on a same radial side of the shaft.

12. The delivery device of claim 10, wherein the first side port and the second side port are on different radial sides of the shaft.

13. The delivery device of claim 10, wherein the first side port and the second side port axially overlap each other.

14. A method comprising:
    inserting a proximal portion of a guidewire through a distal end of a delivery device, into a lumen of the delivery device, and past a flap member of the delivery device, the guidewire being directed by a terminal end of the flap member having a concave shape;
    retracting the guidewire until a distal portion of the guidewire is proximal to the flap member; and
    advancing the guidewire until the flap member directs the distal portion of the guidewire out of the lumen and through a side port of the delivery device.

15. The method of claim 14, further comprising, after the inserting and before the retracting:
    advancing the guidewire to a target anatomy; and
    advancing the delivery device over the guidewire to the target anatomy.

16. The method of claim 15, wherein the target anatomy comprises an occlusion.

17. The method of claim 16, further comprising penetrating a vessel wall adjacent to the occlusion with another device coupled to the guidewire.

18. The method of claim 16, further comprising penetrating the occlusion with an interventional device coupled to the guidewire.

19. The method of claim 14, wherein the flap member is biased to a first position blocking at least a portion of the lumen and away from a second position blocking at least a portion of the side port.

20. The method of claim 19, wherein the inserting transitions the flap member from the second position to the first position.

* * * * *